United States Patent [19]
Chaundy et al.

[11] Patent Number: 5,756,719
[45] Date of Patent: May 26, 1998

[54] DOUBLE EMULSION TECHNIQUES FOR MAKING NOVEL COMPOSITIONS CONTAINING GLUTEN AND POLYSACCHARIDES THAT CONTAIN URONIC ACID RESIDUES USEFUL FOR ENCAPSULATING FATS, OILS AND SOLIDS

[75] Inventors: Frederick K. Chaundy, Gross Ile; Scott P. Melidosian, Allen Park; Rudolph E. Lisa, Gross Ile; Jeffrey L. Finnan, Dearborn, all of Mich.

[73] Assignee: BASF Corporation, Mount Olive, N.J.

[21] Appl. No.: 706,855

[22] Filed: Sep. 3, 1996

[51] Int. Cl.⁶ .............................. C07H 1/00; C07H 13/02
[52] U.S. Cl. .......................... 536/124; 536/2; 536/3; 536/119; 536/123.1
[58] Field of Search .................. 536/2, 3, 119, 536/124, 123.1; 514/54

[56] References Cited

U.S. PATENT DOCUMENTS

| | | | |
|---|---|---|---|
| 3,351,531 | 11/1967 | Yajima | 426/98 |
| 3,786,123 | 1/1974 | Hanssi | 264/53 |
| 4,911,942 | 3/1990 | Yajima | 426/455 |
| 4,935,257 | 6/1990 | Yajima | 426/555 |
| 5,074,902 | 12/1991 | Connick et al. | 504/117 |
| 5,358,863 | 10/1994 | Quimby et al. | 435/178 |
| 5,418,010 | 5/1995 | Janda et al. | 427/213.31 |
| 5,512,268 | 4/1996 | Grinstaff et al. | 424/9.322 |

FOREIGN PATENT DOCUMENTS 918168  2/1963  United Kingdom.

*Primary Examiner*—John Kight
*Assistant Examiner*—Everett White
*Attorney, Agent, or Firm*—Joanne P. Will

[57] ABSTRACT

Method of making compositions comprising gluten and polysaccharides that contain uronic acid residues encapsulating fats, oils and solids comprising double emulsion techniques.

3 Claims, No Drawings

DOUBLE EMULSION TECHNIQUES FOR MAKING NOVEL COMPOSITIONS CONTAINING GLUTEN AND POLYSACCHARIDES THAT CONTAIN URONIC ACID RESIDUES USEFUL FOR ENCAPSULATING FATS, OILS AND SOLIDS

FIELD OF THE INVENTION

The present invention relates to methods for making biodegradable compositions containing gluten and polysaccharides that contain uronic acid residues comprising the use double emulsion techniques. Said compositions are useful for encapsulating administering various ingredients in fat, oil and solid forms, such as flavoring, fragrance and vitamins, vitamin oils, agricultural chemicals, and pharmaceutical agents.

BACKGROUND OF THE INVENTION

Gluten is the protein fraction of the wheat or corn kernel. Specifically, vital wheat gluten is the water-insoluble complex protein fraction separated from wheat or wheat flour. In its freshly extracted wet form it is known as gum gluten which when dried yields a cream-to-tan, free-flowing powder of high protein content and bland taste. When re-hydrated, it regains its original characteristics. So unique is the functionality of wheat gluten and so persistent is the structural integrity after cooking, it is commercially important and it appears to have no functional competitor. Corn gluten or zein has similar chemistry and is also commercially important despite its higher cost.

However, the water insolubility of gluten can limit its usefulness. Commonly, those skilled in the art solubilize gluten using acids or bases. Corn gluten is soluble in some organic solvents, such as alcohols. However, solvent recovery is an issue which adds to the cost of the process. In many such applications, the addition of an acid or base is inconvenient, since they would end up in the solid product, and could resolubilize the gluten, a potentially undesirable result. If an organic acid is used to solubilize gluten, it may be flashed off during drying. This can result in recovery problems to prevent pollution (infact, gluten is dried in just this way). An additional potential method, the use of enzymes to reduce the molecular weight of the gluten and thereby increase the solubility would have other drawbacks--lowering the molecular weight would probably destroy part of the film forming capability of the gluten, making its use less desirable as a protective encapsulator.

Once solubilized, gluten can be used in a wide range of applications. It can be used in film forming (i.e. binding or adhesive properties), it has thermosetting properties, large water absorption capabilities, has bland or slight cereal flavor properties, as well as visco-elastic properties. It's water absorptive properties are used to extend shelf-life of many foods. It is used as a binding and adhesive agent in meats, and is capable of forming glazing meat surfaces. It is used by the baker to adjust flour protein level, and is used for its visco-elastic properties to improve bakery dough strength. It is used to fortify cereal with extra protein, and helps to bind vitamin-minerals in enriched breakfast cereal formulas. Wheat gluten imparts texture and eating quality to synthetic cheeses, and replaces more expensive sodium caseinate in several imitation cheese products. Gluten is also often used in extruded snack foods, tortillas, Japanese surimi, breading, batter mixes, coatings, and flavoring. It is used in canned pet food for binding and moisture absorbing properties. It is used in aquaculture for adhesive properties in granule forms of fish food. Its use is wide and pervasive, in part because it has GRAS status (generally recognized as safe) by the US Food and Drug Administration. Zein or corn gluten has similar properties except it is not viscoelastic and, therefore, not useful in improving bakery dough strength.

Other useful applications for gluten include: encapsulating weed and pest control agents, flavorings, vitamins, medicaments, imaging agents for MRI (Magnetic resonance imaging) usage , preparing fragrance, flavor and vitamin compositions, and sprayable formulations for pest control.

Specifically, EP 0.357,169 B discloses a process for preparing a vitamin powder wherein the vitamin is added to acid- or base-solubilized gluten and then spray dried to form the powder.

GB 918,168 discloses a powdered feed supplement composition wherein vitamin bearing oils are encased within a protective protein shell such as soy flour or gluten. Said feed supplement is prepared by spray drying. Said soy flour or gluten is solvent extracted. U.S. Pat. No. 3,786,123 and 5,418,010, disclose a microencapsulation process wherein the core material (vitamins, minerals, and flavorings in liquid or solid form) is encapsulated with an animal or vegetable protein, such as an acid- or base-solubilized gluten. The encapsulation takes place via an extruder. U.S. Pat. No. 4,911,942 discloses stabilized oil and fat powders wherein said oil or fat is coated with an acid- or base-solubilized gluten. The powder is formed by spray drying or vacuum drying. U.S. Pat. No. 5,512,268 discloses imaging agents for NMRI (nuclear magnetic resonance imaging) encapsulated in gluten which are injectable into the human body. U.S. Pat. No. 5,358,863; 5,074,902, and 5,358,863 all disclose weed and pest control agents encapsulated in gluten. Finally, U.S. Pat. No. 3,351,531 discloses gluten as an encapsulating agent for oil-in-water dispersions. The gluten is solubilized with acetic acid or ammonia before it can be used to encapsulate the oil in water emulsion.

Applicants have now discovered a method of making novel gluten compositions containing polysaccharides that contain uronic acid residues useful for encapsulating fats, oils, and solids utilizing double emulsion techniques. The polysaccharide that contains a uronic acid residue solubilizes the gluten without the need for acids and bases as required by the art. The elimination of the acid or base solubilization allows working at a neutral pH. The process for solubilizing the gluten with a polysaccharide that contains a uronic acid residue is disclosed in the copending continuation in part application entitled: "Improved Process for Solubilizing Gluten That Normally Is Capable of Absorbing Water Without Dissolution", filed Sep. 3 1996, U.S. Ser. No. 08/706,760 which describes a method of solubilizing gluten without the use of acids or bases. It uses polysaccharides that contains uronic acid residues to dissolve the gluten. When gluten is solubilized with a polysaccharide that contains uronic acid residues said gluten is a cost effective substitute for applications requiring gelatin, since gluten is much cheaper than gelatin.

Specifically, this application relates to a method of making compositions comprising oils or solids and gluten and a polysaccharide that contains a uronic acid residue wherein a neutral pH is maintained. Said method employs double emulsion techniques . Since many compounds, such as vitamins, are affected by extremes of pH, a neutral pH is of great utility. Further, acid or base recovery is not an issue and processing costs are reduced.

DEFINITIONS AND USAGES OF TERMS

The term "beadlet" as used herein refers to substantially spherical particles which are primarily between about 105 microns and about 840 microns in diameter.

The term "free flowing" as used herein refers to powders or beadlets having a FLODEX flowability of 50 or more. The FLODEX flowability test is described in detail in U.S. Pat. No. 5,000,888, column 7, lines 45–70, column 8, lines 1–45, incorporated by reference herein

SUMMARY

A method of making a composition useful for encapsulating fats, oils and solids comprising:
- (a) 14.5 to 97% gluten;
- (b) a polysaccharide that contains uronic acid residues, wherein said polysaccharide that contains uronic acid residues is at least 3% of the level of the gluten
- (c) 0.0 to 95% water;

comprising the steps of:
  a. preparing an aqueous solution of a polysaccharide that contains uronic acid residues and gluten, and a gelling binder,
  b. preparing a primary emulsion by homogenizing said aqueous solution of a polysaccharide that contains uronic acid residues and gluten with oil to form an oil in water emulsion.
  c. preparing a secondary emulsion by adding said primary emulsion to water insoluble liquid with agitation.
  d. gelling the mixture formed in (c) to form discrete beadlets by cooling said primary emulsion/water insoluble liquid composition.
  e. adding a powdery coating agent to coat the beadlets in the mixture formed in (d),
  f. filtering the coated beadlets from the water insoluble liquid,
  g. washing and drying said coated beadlets A method of making a composition useful for encapsulating fats, oils and solids comprising:
- (a) 14.5 to 97% gluten;
- (b) a polysaccharide that contains uronic acid residues, wherein said polysaccharide that contains uronic acid residues is at least 3% of the level of the gluten
- (c) 0.0 to 95% water;

comprising the steps of:
  a. preparing an aqueous solution of a polysaccharide that contains uronic acid residues and gluten,
  b. preparing a primary emulsion by homogenizing said aqueous solution of a polysaccharide that contains uronic acid residues and gluten with oil to form an oil in water emulsion.
  c. adding a gelling salt to said primary emulsion.
  d. preparing a secondary emulsion by adding said primary emulsion to water insoluble liquid with agitation until gelling occurs and discrete beadlets are formed,
  e. adding a powdery coating agent to coat the beadlets in the mixture formed in (d).
  f. filtering the coated beadlets from the water insoluble liquid,
  g. washing and drying said coated beadlets All percentages are on a weight percent basis unless otherwise indicated.

DETAILED DESCRIPTION

A method of making a composition useful for encapsulating fats, oils and solids comprising:
- (a) 14.5 to 97% gluten;
- (b) a polysaccharide that contains uronic acid residues, wherein said polysaccharide that contains uronic acid residues is at least 3% of the level of the gluten
- (c) 0.0 to 95% water;

comprising the steps of:
  a. preparing an aqueous solution of a polysaccharide that contains uronic acid residues and gluten, and a gelling binder,
  b. preparing a primary emulsion by homogenizing said aqueous solution of a polysaccharide that contains uronic acid residues and gluten with oil to form an oil in water emulsion.
  c. preparing a secondary emulsion by adding said primary emulsion to water insoluble liquid 1 with agitation.
  d. gelling the mixture formed in (c) to form discrete beadlets by cooling said primary emulsion/water insoluble liquid composition.
  e. adding a powdery coating agent to coat the beadlets in the mixture formed in (d),
  f. filtering the coated beadlets from the water insoluble liquid,
  g. washing and drying said coated beadlets A method of making a composition useful for encapsulating fats, oils and solids comprising:
- (a) 14.5 to 97% gluten;
- (b) a polysaccharide that contains uronic acid residues, wherein said polysaccharide that contains uronic acid residues is at least 3% of the level of the gluten
- (c) 0.0 to 95% water; comprising the steps of:
  a. preparing an aqueous solution of a polysaccharide that contains uronic acid residues and gluten,
  b. preparing a primary emulsion by homogenizing said aqueous solution of a polysaccharide that contains uronic acid residues and gluten with oil to form an oil in water emulsion.
  c. adding a gelling salt to said primary emulsion.
  d. preparing a secondary emulsion by adding said primary emulsion to water insoluble liquid with agitation until gelling occurs and discrete beadlets are formed,
  e. adding a powdery coating agent to coat the beadlets in the mixture formed in (d),
  f. filtering the coated beadlets from the water insoluble liquid,
  g. washing and drying said coated beadlets Fats and Oils Useful in the Practice of the Present Invention Fats and oils useful in the practice of the present invention include, but are not limited to, flavoring and fragrance oils, vegetable oils, fats, and natural and synthetic vitamins such as A,D,E and K. Preferably, the oils are vitamin oils such as A, D, E, and K. The most preferred vitamin oils are A and D. Said fats and oils are used at levels of 0.01–85% , more preferably, 0.01–70% and most prefearbly 0.01–40% by weight.

Solids Useful in The Practice of the Present Invention

Solids useful in the practice of the present invention include agricultural chemicals including pesticides, herbicides, fungicides, growth regulators, and fertilizers, solid forms of natural and synthetic vitamins such as C and B vitamins, including, but not limited to, folic acid, riboflavin, pyridoxine, thiamine, and niacin. Other suitable solids include, animal fats and solid pharmaceuticals.

Representative solid pharmaceuticals include, but are not limited to: antiinfectives such as antibiotics, and antiviral agents, analgesics, anorexics, antihelminthics, anti arthritics, antiasthmatics, anticonvulsants, antidepressants, antidiabetic agents, antidiarrheals, antihistamines, antiinflammatory agents, antimigraine preparations, anti nauseants, antineoplastics, antiparkinsonism drugs, antipruritics, antipsychotics, antipyretics, antispasmodics, anticholinergics, sympathomimetics, xanthine derivatives, cardiovascular preparations including calcium channel blockers, and beta blockers, and anti arrythmics, antihypertensives, diuretics, vasodilators including general coronary, peripheral and cerebral, central nervous system stimulants, cough and cold preparations including decongestants, hormones such as estradiol, and other steroids, including corticosteroids, hypnotics, immunosupressives, muscle relaxants, para sympatholytics, psychostimulants, sedatives and tranquilizers.

Pharmaceutical compounds representative of the classes stated hereinabove are described in "Goodman and Gilman's, The Pharmacological Basis of Therapeutics", 8th edition.

In a particularly preferred embodiment of the present invention, the antihistamine chlorpheniramine maleate is encapsulated in gluten and spray dried to a free-flowing according to the methods described herein and in 2 copending applications "Novel Compositions Containing Gluten and Polysaccharides that Contain Uronic Acid Residues Useful for Encapsulating Fats, Oils and Solids" and "Spray Techniques for Making Novel Compositions Containing Gluten and Polysaccharides that Contain Uronic Acid Residues Useful For Encapsulating Fats, Oils and Solids" filed concurrently Sep. 3, 1996 U.S. Ser. Nos. 08/697, 935respectively. The spray dried chlorpheniramine maleate encapsulated in gluten can be blended with other pharmaceutical excipients and carriers known to those skilled in the art, and is suitable for tabletting.

Representative agricultural chemicals include, but are not limited to, S-2,3,3-trichlorallul di-isopropyl(thiocarbamate) (tri-allate) and 3,6-dichloropyridine-2-carboxylic acid (3,6dichloropicolinic acid), esters of (±)-2[4-(5-trifluoromethyl-2-pyridyloxy)phenoxy]propionic acid (Fluazifop), the butyl ester thereof (Fluazifop butyl) and esters of (±)-2[4-(3-chloro-5-trifluoromethyl-2-pyridyloxy)-phenoxy]propionic acid (Dowco 453) such as the ethoxyethyl ester thereof.

Other suitable herbicides are derivatives of urea, carboxylic acid ester, amino-acids, diphenylethers, phenylcarbamates, s-triazine, as-triazinones, heterocycles, s-triazinddiones, phenylpyridaziones, benzofuran, quinoline carboxylic acids, phenoxy acetic acids phenoxy propionic acids, and benzene sulphonamides.

Examples of herbicidally active ureas are:
3-(3-chloro-p-toly)-1,1 dimethylurea (Chlortoluron),3-(4-isopropylphenyl)1,1 dimethylurea
(Isoproturon), 3-(3,4-dichlorophenyl)-I-methoxy-1-methylurea (Linuron),
1-(benzothiazol-2-yl)-1,3-dimethylurea (methabenzthiazuron), and
3-(3-chloro-4-methoxyphenyl)-1,1-dimethylurea) (Metoxuron).

Examples of herbicically active carboxylic acid esters are:
ethyl N-benzoyl-N-(3,4-dichlorphenyl)-DL-alaninate (Benzoylprop-ethyl), isopropyl N-benzoyl-N-(3-chloro-4-fluorophenyl)-DL-alaninate (Flamprop-isopropyl), and methyl N-benzoyl-N-(3-chloro-4-fluorophenyl)-DL-alaninate (Flamprop-methyl), esters of (±)-2-[4-(3-chloro-5-trifluoromethyl-2-pyridyloxy)phenoxy] propionic acid (Dowco 453), esters of (±)-2-[4-(6-chlorobenzothiazol-2-yloxy)-phenoxy]propionic acid (Fenthiaprop), such as the ethyl ester (Fenthiaprop-ethyl) esters of (±)-2-[4-6-chlorobenzoxazol-2-yloxy)phenoxy] propionic acid (Fenoxaprop), such as the ethyl esters (Fenoxaprop-ethyl),
(±)-2-[4-3,5-dichloro-pyridyloxy)phenoxy]propionic acid-2-benzyloxy-esters, methyl 3-[1-(allyloxyimino)butyl]-4-hydroxy-6,6- dimethyl-2-oxocyclohex-3-ene carboxylate (Alloxydim) and lower esters of phenoxy acetic acid and phenoxy propionic acid such as 2,4-D, MCPA, Dichlorprop and Mecoprop.

Examples of herbicidally active amino acids are:
N-(phosponomethyl)glycine (Glyphosate) as acid or in salt form, and (±)-2-amino-4-(hydroxymethylphosphinyl) butanoic acid (Glufosinate) as acid or in salt form.

Examples of herbicidally active diphenylethers are:
2,4-dichlorophenyl-4-nitrophenyl ether (Nitrofen), and 5-(2-chloro-a,a,a-trifluoro-p-tolyloxy)-2-nitrobenzoic acid (Acifluorfen).

Examples of herbicidally active phenylcarbamates are:
3-[(methoxycarbonyl)aminophenyl)amino]phenyl-N-(3'-methyl-phenyl)carbamate (Phenmedipham), and
ethyl 3-phenylcarbamoyloxyphenylcarbamate (Desmedipham).

Examples of herbicidally active s-triazines are:
2-(4-chloro-6-ethylamino-1,3,5-triazin-2-ylamino)-2-methylpropionitrile (Cyanazine),
2-chloro-4,6-bis(ethylamino)-1,3,5-trazine (Simazine),
2-tert-butylamino-4-ethylamino-6-methylthio-1,3,5-triazine (Terbutryne), and
2-chloro-4-ethylamino-6-isopropylamino-1,3,5-triazine (Atrazine).

Examples of herbicidally active as-triazin-5-ones are:
4-amino-4,5-dihydro-3-methyl-6-phenyl-1,2,4-triazin-5-one (Metamitron),
6-tert-butyl-4-isobutylideneamino-3-methylthio-1,2,4-triazin-5(4H)-one (Isomethiozin), and
6-tert-butyl-4-isobutylideneamino-3-methylthio-1,2,4-triazin-5(4H)-one (Isomethiozin), and
4-amino-6-tert-butyl-4,5-dihydro-3-methylthio-1,2,4-triazin-5-one (Metribuzin).

An example of herbicidally active heterocyclic compounds is:
3-isopropyl-1-(H)-benzo-2,1,3-thiadiazin-4-one-2,2-dioxide (Bentazone).

An example of herbicidlly active s-triazindiones is:
3-cyclohexyl-6-dimethylamino-1-methyl-1,3,5-triazine-2,4 (1H,3H)-dione (Hexazione).

An example of herbicidally active sulfonamides is:
1-(2-chlorophenylsulphonyl-3-(4-methoxy-6-methyl-1,3,5-triazine-2-yl)urea (Chlorsulfuron).

An example of herbicidally active phenylpyridazinones is:
5-amino-4-chloro-2-phenyl-3(2H)pyridazinone (Chloridazon).

An example of herbicidally active benzofurans is:
(±)-2-ethoxy-2,3-dihydro-3,3-dimethylbenzofuran-5-yl methanesulphonate (Ethofumesate).

Examples of herbicidally active phenoxy acetic acids and phenoxy propionic acids are:
2,4-dichlorophenoxy acetic acid (2,4-D)
4-chloro-2-methylphenoxy acetic acid (MCPA)
(±)-2-(2,4-dichlorophenoxy)propionic acid (Dichlorprop)
(±)-2-(4-chloro-2-methylphenoxy)propionic (Mecoprop) and
(±)-2-[4-(4-chlorophenoxy)phenoxy]propionic acid.

In compositions comprising the above-mentioned active acids, at least part of the acids may be present in salted form.

An example of herbicidally active active quinoline carboxylic acids is: 7-chloro-3-methyl-quinoline-8-carboxylic acid (BASF 518H).

Other suitable agricultural chemicals useful in the practice of the present invention are described in "The Herbicide Handbook", published by Weed Science Society of America, 7th edition, incorporated by reference herein.

Preferably, solids are used at levels of 0.01 to 85%, more preferably 0.01 to 70%, most preferably 0.01 to 40%.

Gluten Useful in the Practice of the Present invention

Gluten useful in the practice of the present invention includes wheat and corn gluten.

Wheat is preferred because of its low cost

Both wheat and corn gluten are suitable for encapsulating fats, oils, and solids.

Wheat gluten is preferred because of its low cost. However, corn gluten is particularly suited for use in preparing edible compositions for those allergic to wheat gluten, e.g. Celiac sprue patients.

Preferably, gluten is used at levels of 14.5 to 97%, more preferably 30 to 60%, most preferably 40 to 70%

Polysaccharides That Contain Uronic Acid Residues Useful in Solubilizing Gluten Polysaccharides that contain uronic acid residues useful in solubilizing gluten are described in the copending continuation in part (CIP) application entitled "Improved Process for Solubilizing Gluten That Normally Is Capable of Absorbing Water Without Dissolution", filed Sep. 3, 1996, U.S. Ser. No. 08/706,760 which describes a method of solubilizing gluten using a polysaccharide that contains uronic acid residues. Said CIP is incorporated by reference herein.

Specifically, useful polysaccharides that contain uronic acid residues include, but are not limited to low methoxyl pectins, algin, gum arabic, gum tragacanth, gum karaya, gum ghatti, xanthan gum, gellan gum, seed mucilages.

Said polysaccharides that contain uronic acid residues are used at a level of at least 3% of the level of gluten, preferably at a level of 3 to 150% of the level of gluten, more preferably at a level of 3 to 75% of the level of gluten, and most preferably at a level of 3 to 20% of the level of gluten Optional Ingredients Useful in the Compositions of the Present Invention Optional ingredients useful in the present invention include, but are not limited to, resins, fillers, binders, lubricants, solvents, glidants, disintegrants, co solvents, surfactants, preservatives, sweetening agents, flavoring agents, buffer systems, pharmaceutical grade dyes or pigments and viscosity agents.

Flavoring agents useful herein include, but are not limited to, those described in Remington's Pharmaceutical Sciences, 18th Edition, Mack Publishing, 1990, pp1288–1300 and Furia and Pellanca, Fenaroli's Handbook of Flavor Ingredients, The Chemical Rubber Company, Cleveland, Ohio, 1971. A compilation of suitable flavorings can also be found in the Code of Federal Regulations, at 21 CFR Parts 170–197.

Dyes or Pigments useful in the present invention include those described in the Handbook of Pharmaceutical Excipients, pp81–90, 1986 by the American Pharmaceutical Association and the Pharmaceutical Society of Great Britain.

Preferred cosolvents include, but are not limited to, ethanol, glycerin, propylene glycol, polyethylene glycols.

Preferred buffer systems include, but are not limited to, acetic, boric, tartaric, carbonic, succinic, maleic, citric, acetic, benzoic, phosphoric, lactic, glyceric, glutaric, and glutamic acids and their sodium, potassium and ammonium salts.

Preferred surfactants include, but are not limited to, polyoxyethylene sorbitan fatty acid esters, polyoxyethylene monoalkyl ethers, sucrose monoesters, lanolin esters, alkyl sulfate salts.

Preferred preservatives include, but are not limited to, phenol, alkyl esters of parahydroxybenzoic acid, o-phenylphenol benzoic acid, citric acid, boric acid, sorbic acid, chlorobutanol, benzyl alcohol, thimerasol, phenylmercuric acetate, benzalkonium chloride, cetylpyridinium chloride, and methyl paraben and propyl paraben.

Preferred sweeteners include, but are not limited to, sucrose, glucose, saccharin, sorbitol, mannitol, aspartame.

Preferred viscosity agents include, but are not limited to, the water soluble celluloses such as methyl cellulose, sodium carboxymethylcellulose, hydroxypropyl cellulose, hydroxymethyl cellulose, and ethyl cellulose and hydroxyethyl cellulose.

Preferred fillers include, but are not limited to, lactose, mannitol, sorbitol, tribasic calcium phosphate, compressible sugar, starch, calcium sulfate, dextro and microcrystalline cellulose.

Preferred lubricants include, but are not limited to, magnesium stearate, stearic acid, and talc.

Preferred glidants include, but are not limited to, talc and colloidal silicon dioxide.

Preferred disintegrants include, but are not limited to, starch, sodium starch glycolate, crospovidone, croscarmelose sodium, and microcrystalline celullose.

Preferred binders include, but are not limited to, hydroxypropyl cellulose, pregelatinized starch, gelatin, povidone, hydroxypropylmethyl cellulose, methylcellulose, sucrose, sorbitol, and ethylcellulose.

Optional ingredients are used at a level of 0 to 95%. Preservatives and antioxidants are useful in the compositions of the present invention at levels of 0–5%.

Preservatives and antioxidants such as, but not limited to, parabens and citric acid are also useful in the compositions of the present invention at levels of 0–5%

Making the Composition of Present Invention

The gluten is solubilized according to the methods described in US CIP application entitled "Improved Process for Solubilizing Gluten That Normally Is Capable of Absorbing Water Without Dissolution", filed Sep. 3, 1996U.S. Ser. No. 08/706,760 and incorporated by reference herein. The gluten solubilized with a polysaccharide that contains uronic acid residues is prepared as described in the said CIP application. The solid or liquid is then added to prepare the compositions of the present invention according to the methods described hereinbelow. Further, a composition application and a spray drying method for making the composition of the present invention are the subjects of 2 co-pending applications entitled "Novel Compositions Containing Gluten and Polysaccharides That Contain Uronic Acid Residues Useful for Encapsulating Fats, Oils and Solids" and "Spray Techniques for Making Novel Compositions Containing Gluten and Polysaccharides That Contain Uronic Acid Residues Useful for Encapsulating Fats, Oils and Solids", respectively, filed concurrently with the present application on Sep. 3, 1996 U.S. Ser. Nos. 08/697,939 and 08/697,935, respectively.

The emulsion of gluten, polysaccharides that contain uronic acid residues, preferably pectins and alginates that gel in the presence of polyvalent cations, and the oil or solid, is sprayed into a blender containing agitated inert carrier, or a carrier part of which will react to coagulate the gluten. The carrier can be any number of inert powders, including starch, modified starch, silica, aluminum silicates, etc. It is however preferred to include a coagulating agent for the dissolved gluten, a salt containing calcium, such as calcium acetate. The liquid emulsion is sprayed in while the blender is agitating the carrier contents, and small particles are formed.

The powder can then be dried in the blender, or by alternate means, and the excess carrier removed from the dry powder.

The compositions of the present invention prepared by the methods described herein preferably have a FLODEX measurement of 50–500, more preferably 100–500, most preferably 200 to 500.

General Discussion of Methods of Encapsulation

Spray Drying

Spray drying is a common method of encapsulating oils or solids and is well known to those skilled in the art. This type of encapsulation is done for a variety of reasons such as to make liquids into powders, protect encapulants from degradation, and to slow the release of the encapsulatants. Typically, an emulsion is prepared by dissolving the binder which is typically a hydrocolloid such as gelatin, water-soluble starch, or a water-soluble cellulose and other ingredients such as fillers surfacts etc, then the oil or solid is added and emulsified in the case of an oil or dispersed in the case of a solid into the solution of the binder. The emulsion or dispersion is then pumped to a spray drying chamber and atomized into small droplets by one of several methods. The atomized droplets contact hot air (usually above 150° C.) that is conveyed into the drying chamber by blowers and the water is evaporated, leaving a powder which consists of fine oil droplets in a matrix of dry encapsulating agent. This particular method usually produces relatively small particles compared to other methods. However, it is sometimes desirable to make a larger particle since the oil or solid is better stabilized against the chemical and temperature extremes of many manufacturing processes or end-use environments. Additionally, since the spray-drying processes is very rapid, the powders particles tend to be porous due to the rapid evaporation of the water. Also, the protective binders do not get much time to align and bond to each other to form as strong protective matrix as is possible. A spray drying process has an upper limit to the particle size that can be produced. As the particles become larger, the droplet dries more slowly owing to the reduction in particle surface area per unit volume from which the evaporation needed to dry the particle takes place. If the particles are too large they will impact the walls of the dryer still wet and will stick, leading to tower build up and poor yields. To further increase the particle size, and provide more stability when needed, an alternate method must be used to produce the particle.

Spray Congealing

If the encapsulating binder is capable of gelling, spray cooling, also known as spray congealing, can be employed. It is well known in the art that gelatin emulsions can be sprayed into a fluidized cloud or bed of starch or into a cloud of hydrophobic silica or other coating agent such that the resultant starch or silica coating prevents the liquid particles from sticking to each other. Subsequent to the particle formation, they are dried utilizing methods known to those skilled in the art, including but not limited to, fluid bed drying, rotary vacuum drying, ribbon blender drying, flash drying and mechanical fluidized bed drying, with what is typically ambient or at least lower temperature air than the spray drying process. A gelling binder such as gelatin is needed so that the liquid droplets, after they are coated, gel and gain some mechanical strength so that they remain intact as they are dried according to methods known to those skilled in the art, including but not limited to, fluid bed drying, rotary vacuum drying, ribbon blender drying, flash drying or mechanical fluidized bed drying. As an alternative to to a gelling hydrocolloid, it is possible to add appropriate ingredients that will over time react to provide a gel such as calcium salts with pectins and alginates. Since the drying is much slower, generally hours at a time, the beadlets which are generally much larger than those made via traditional spray drying are less porous than spray-dried powders. And, the slow drying allows some of the binders to hydrogen bond to each other to form a tighter protective matrix then that achievable with traditional spray drying. In the case of starch coated beadlets, the starch coating itself can provide an additional protective barrier.

Modified Spray Drying

As stated above, to be able to spray congeal, the binders need to be able to gel to provide mechanical strength to survive the early stages of fluid-bed drying. For those cases where the larger and less porous beadlets are needed but the binders are incapable of gelling, modified spray drying can be incorporated. Modified Spray drying of oils or solids is also known to those skilled in the art and has been well described, in U.S. Pat. No. 5,460,823, incorporated by reference herein. In the modified spray drying process the suspension is preferably sprayed at a temperature of from 5° to 99° C. and at a viscosity of from 50 to 300 mPa using an atomizing nozzle or an atomizing wheel in 95° C. A por, wherein the temperature is from 50° to 95° C. A powdery spraying excipient may be blown into the spraying chamber in order to prevent agglomeration of the formed microcapsules and to prevent adherence to the chamber wall. The spraying excipient is preferably supplied in an amount of from 5 to 50 percent by weight based on the weight of the final product. The powdered microcapsules may be transferred to a fluidized bed, wherein they may be transferred to a fluidized bed, wherein they may be dried to a residual water content of between 0 to 10% (preferably from 2 to 5%) and excessive spraying excipient is separated. The drying air temperature is preferably from about 0° to about 60° C.

Spray Formulation

Another variation of modified spray drying and spray congealing is the use of a hydrophic silica to coat the outside of the newly formed wet beadlets instead of starch. This process is generally referred to as spray formulation. An older technique, that is sometimes performed particularly in laboratories where the availability of suitable spraying systems is limited, is the double emulsion technique. In this process, a primary emulsion is prepared as already described. This emulsion is then dispersed in hot mineral oil. Thus a oil-in-water-in-oil emulsion (double emulsion) is formed. This mix is cooled until the primary (aqueous) emulsion has congealed and typically a powdery coating agent is added to prevent sticking of the beadlets. After coating, the beadlets are filtered an washed with a low boiling petroleum solvent to remove the residual mineral oil. These washed beadlets are then air dried.

In the above processes the binders typically provide adequate protection to the encapsulants as long as they powders and not exposed to high moisture or wet conditions particulary in the presence of mechanical stress. In such cases the protective binders will soften or dissolve if enough water is present. If so, they the powders or beadlets can fall apart. If the these are exposed to pelleting or extrusion processes that are commonly employed in feed, food, and some other agricultural applications, high moisture, steam, and severe mechanical stress are employed. In such cases the protective powders are substantially destroyed, and sensitive encapsulants can be destroyed or layed open to quick degradation on storage. It is already known in the art that gelatin-based beadlets made can be made substantially water-insoluble by chemical and thermal crosslinking. This requires additional processing and can be somewhat detrimental to the encapsulants during this processing.

General Discussion of Double Emulsion Techniques for Encapsulating Oils and Solids of the Present Invention While knowledge of these processes clearly exists, it is not taught that the compositions containing gluten and polysaccharide containing uronic acid residues, useful for encapsulating oils and solids, can be prepared by double emulsion techniques. Further, it is it is not taught in the art that the gluten solubilized with polysaccharides that contain uronic acid residues which is prepared according to double emulsion techniques described herein will remain insoluble, and thus, an optimal encapsulating agent The following non limiting examples illustrate the double emulsion techniques of the present invention.

Example 1

Preparing a Vitamin Powder via Double Emulsion Process with Gelatin 200 grams of water are heated with a hot plate in a 600-ml beaker to about 50° C. as 25 grams of a gelling agent, such as gelatin (Sanofi Type A, Pork Skin), is added. Once the gelatin is dissolved, the beaker is removed from the heat and cooled to about room temperature. To the gelatin solution three grams of algin (Kelco Kelgin x1/f) is added while agitating. Next, 40 grams of gluten are mixed in with a high shear mixer. An additional 50 grams of water are added to reduce viscosity. The primary emulsion is formed by adding 680 grams of vitamin A acetate oil (1.8 million i.u./gram) to this mixture and is homogenized with the high shear mixer as the temperature rises from 45° C. to 60° C. The secondary emulsion is formed by adding the primary emulsion to 400 grams of a water insoluble liquid such as light mineral oil maintained at 60° C. in a round-bottom flask. This mixture is agitated enough so that the aqueous emulsion droplets are about 100 microns in size in the mineral oil. The flask is then placed in an ice-water bath. When the temperature of the mixture reaches about 20° C. the agitation is slowed to that enough to maintain a suspension. When the mixture reaches 6° C., 26 grams of a powdery coating agent such as Dryflo® (hydrophobic) corn starch is added. After about five minutes, the mixture was diluted with about an equal volume of petroleum ether (boiling point 60°–90° C.). This mixture is poured into a fritted-glass filter which was connected to a filter flask under reduced pressure. The filtered beadlets are washed with three more volumes of petroleum ether. After completely draining, the beadlets are dried by blowing a gentle stream of nitrogen through the bottom of the filter. The next day the lose clumps of beadlets were broken up on 20-mesh screen. The beadlets were subjected to the boiling test as desribed above and the beadlets are substantially insoluble.

Example 2

Preparing a Vitamin Powder via Double Emulsion Process with a Precipitating Salt To 200 grams of water three grams of algin (Kelco Kelgin x1/f) are added while agitating. Next, 40 grams of gluten are mixed in with a high shear mixer. The primary emulsion is formed by adding 680 grams of vitamin A acetate oil (1.8 million i.u./gram) to this mixture and is homogenized with the high shear mixer as the temperture rises from 45° C. to 60° C. Next 1 gram of a gelling salt such as dicalcium phosphate is added and mixed for one minute. The secondary emulsion is formed by adding the primary emulsion to 400 grams of a water insoluble liquid such as light mineral oil maintained at 60° C. in a round-bottom flask. This mixture is agitated enough so that the aqueous emulsion droplets are about 100 microns in size in the mineral oil. The mixture is kept at 60° C. for 20 minutes after which the agitation is slowed enough to maintain a suspension. The flask is then placed an ice-water bath. When the temperature of the mixture reaches about 20° C., 26 grams of a powdery coating agent such as Dryflo®(hydrophobic) corn starch are added. After about five minutes, the mixture is diluted with about an equal volume of petroleum ether (boiling point 60°–90° C.). This mixture is poured into a fritted-glass filter which is connected to a filter flask under reduced pressure. The filtered beadlets are washed with three more volumes of petroleum ether. After completely draining, the beadlets are dried by blowing a gentle stream of nitrogen through the bottom of the filter. The next day the lose clumps of beadlets are broken up on 20-mesh screen. The beadlets are subjected to the boiling test as desribed above and the beadlets are substantially insoluble.

The beadlets prepared by the methods described herein preferably have a FLODEX measurement of 50–500, more preferably 100–500, most preferably 200 to 500

Utility of the Present Invention

Fats, oils, and solid ingredients encapsulated in gluten solubilized in polysaccharides that contain uronic acid residues can be used to formulate sprayable agricultural formulations, powdered vitamin and pharmaceutical products. Further, unpleasant tasting ingredients such as pharmaceuticals can be encapsulated for taste-masking purposes. Also, said fats, oils, and solids encapsulated in gluten solubilized in polysaccharides containing uronic acid residues can be subject to the harsh conditions of extrusion and pelleting techniques known to those skilled in the art. Moreover, fats, oils, and solid ingredients encapsulated in gluten solubilized in polysaccharides that contain uronic acid residues are useful for preparing time-release formulations for pharmaceutical and agricultural applications. Finally, the compositions need not be spray dried and can be used to formulate liquid formulations of fats, oils and solids.

The following non-limiting examples illustrate the utility of the present invention Utility Example 1

A powdered pharmaceutical composition comprising solid pseudoephedrine encapsulated in gluten and polysaccharides containing uronic acid residues is prepared according to methods described herein Said composition can be blended with the optional ingredients described herein, and tabletted according to methods known to those skilled in the pharmaceutical arts Utility Example 2

A powdered herbicidal composition comprising acifluorfen encapsulated in gluten and polysaccharides containing uronic acid residues is prepared by methods described herein. Said composition is dusted on post emergent crops. By adjusting the various ingredients in the composition, appropriate time-release properties can be obtained.

Utility Example 3

A vitamin encapsulated in gluten and polysaccharides containing uronic acid residues can be blended with optional ingredients as described herein, and tabletted. Also, it can be left in powdered form and is useful as a dietary supplement. The encapsulation provides enhanced stability and taste-making properties for the vitamin.

One skilled in the art understands that the composition of the present invention can be blended with any of the active and inert ingredients described herein and subsequently subjected to extrusion and pelleting processses known to those skilled in the art to produce products in forms acceptable for specific uses, e.g. tablets or pellets.

We claim:

1. A method of making a composition useful for encapsulating fats, oils and solids comprising:

(a) 14.5 to 97% gluten;

(b) a polysaccharide that contains uronic acid residues, wherein said polysaccharide that contains uronic acid residues is at least 3% of the level of the gluten (c) 0.0 to 95% water; comprising the steps of:
 a. preparing an aqueous solution of a polysaccharide that contains uronic acid residues and gluten, and a gelling binder,
 b. preparing a primary emulsion by homogenizing said aqueous solution of a polysaccharide that contains uronic acid residues and gluten with oil to form an oil in water emulsion,
 c. preparing a secondary emulsion by adding said primary emulsion to a water insoluble liquid with agitation,
 d. gelling the mixture formed in (c) to form discrete beadlets by cooling said primary emulsion/water insoluble liquid composition,
 e. adding a powdery coating agent to coat the beadlets in the mixture formed in (d),
 f. filtering the coated beadlets from the water insoluble liquid,
 g. washing and drying said coated beadlets.

2. A method of making a composition useful for encapsulating fats, oils and solids comprising:

(a) 14.5 to 97% gluten;

(b) a polysaccharide that contains uronic acid residues, wherein said polysaccharide that contains uronic acid residues is at least 3% of the level of the gluten (c) 0.0 to 95% water;

comprising the steps of:
 a. preparing an aqueous solution of a polysaccharide that contains uronic acid residues and gluten,
 b. preparing a primary emulsion by homogenizing said aqueous solution of a polysaccharide that contains uronic acid residues and gluten with oil to form an oil in water emulsion,
 c. adding a gelling salt to said primary emulsion,
 d. preparing a secondary emulsion by adding said primary emulsion to water insoluble liquid with agitation until gelling occurs and discrete beadlets are formed,
 e. adding a powdery coating agent to coat the beadlets in the mixture formed in (d),
 f. filtering the coated beadlets from the water insoluble liquid,
 g. washing and drying said coated beadlets.

3. A method for encapsulating fats, oils and solids comprising encapsulating said fats, oils, and solids with a composition comprising:

(a) 14.5 to 97% gluten;

(b) a polysaccharide that contains uronic acid residues, wherein said polysaccharide that contains uronic acid residues is at least 3% of the level of the gluten;

(c) 0.0 to 95% water wherein said encapsulating method comprises the steps of:
 a. preparing an aqueous solution of a polysaccharide that contains uronic acid residues and gluten,
 b. preparing a primary emulsion by homogenizing said aqueous solution of a polysaccharide that contains uronic acid residues and gluten with oil to form an oil in water emulsion,
 c. adding a gelling salt to said primary emulsion,
 d. preparing a secondary emulsion by adding said primary emulsion to water insoluble liquid with agitation until gelling occurs and discrete beadlets are formed,
 e. adding a powdery coating agent to coat the beadlets in the mixture formed in (d),
 f. filtering the coated beadlets from the water insoluble liquid,
 g. washing and drying said coated beadlets.

* * * * *